United States Patent [19]

Rohr

[11] 4,394,222
[45] Jul. 19, 1983

[54] METHOD FOR DETERMINING THE OXYGEN CONTENT IN GASES, UNINFLUENCED BY TEMPERATURE VARIATIONS

[75] Inventor: Franz-Josef Rohr, Abtsteinach, Fed. Rep. of Germany

[73] Assignee: Brown, Boveri & Cie AG, Mannheim-Käfertal, Fed. Rep. of Germany

[21] Appl. No.: 208,432

[22] Filed: Nov. 19, 1980

[30] Foreign Application Priority Data

Nov. 20, 1979 [DE] Fed. Rep. of Germany ....... 2946775

[51] Int. Cl.$^3$ .......................................... G01N 27/46
[52] U.S. Cl. ................................. 204/1 T; 204/406; 204/408; 204/410; 204/411; 204/412; 204/427
[58] Field of Search ................ 204/1 S, 1 T, 195 S, 204/195 R

[56] References Cited

U.S. PATENT DOCUMENTS

| | | | |
|---|---|---|---|
| 3,119,757 | 1/1964 | Schroeder | 204/113 |
| 3,296,113 | 1/1967 | Hansen | 204/195 R |
| 3,539,455 | 11/1970 | Clark | 204/195 P |
| 3,616,274 | 10/1971 | Eddy | 204/195 S |
| 3,691,023 | 9/1972 | Ruka et al. | 204/1 S |
| 3,738,341 | 6/1973 | Loos | 204/195 S |
| 3,791,937 | 2/1974 | Besson et al. | 204/195 S |
| 3,923,624 | 12/1975 | Beekmans et al. | 204/195 S |
| 3,962,866 | 6/1976 | Neidhard et al. | 204/195 S |
| 4,129,491 | 12/1978 | Obiaya | 204/195 S |
| 4,134,818 | 1/1979 | Pebler | 204/195 S |
| 4,169,778 | 10/1979 | Mann et al. | 204/195 S |
| 4,231,733 | 11/1980 | Hickam et al. | 204/195 S |
| 4,244,918 | 1/1981 | Yasada et al. | 204/195 S |

Primary Examiner—T. Tung
Attorney, Agent, or Firm—Herbert L. Lerner; Laurence A. Greenberg

[57] ABSTRACT

Determining the oxygen content in gases, particularly combustion exhaust gases, uninfluenced by temperature variations of the gases by passing the gases into a first electrical measuring cell having a solid electrolyte and electrodes connected to a current source. A diffusion-limited electric current flow dependent on the oxygen content of the gases is obtained and measured as a first electrical signal. Passing an auxiliary gas with constant oxygen content into a second measuring cell similar to the first cell and under the same conditions and obtaining a second electrical signal. The quotient of the two electrical signals is a measure of the oxygen content of the gases uninfluenced by temperature variations of the gases.

4 Claims, 6 Drawing Figures

METHOD FOR DETERMINING THE OXYGEN CONTENT IN GASES, UNINFLUENCED BY TEMPERATURE VARIATIONS

BACKGROUND OF THE INVENTION

1. Field of the Invention

The invention relates to a method and apparatus for determining the oxygen content in gases, particularly combustion exhaust gases, uninfluenced by temperature variations, using at least one first electrochemical measuring cell which is heated to the operating temperature and is connected to a current source, through which a diffusion-limited electric current flows which depends on the oxygen content of the gas, and the magnitude of which is determined as a first electrical signal imaging the oxygen content of the gas.

2. Description of the Prior Art

In one known method of this kind, the electrochemical measuring cell is provided with a solid electrolyte which has electrodes on opposite surfaces. The electrode serving as the cathode is acted upon by the gas to be measured, wherein the oxygen content of the gas diffuses into the electrode and is reduced to oxygen ions which are transported through the solid electrolyte to the opposite electrode and are oxidized there to oxygen molecules. The electric current flowing with the oxygen ions through the solid electrolyte is a measure for the oxygen content of the gas. The rate at which the oxygen diffuses into the electrode is a function of the oxygen content of the gas to be measured so that the electric current flowing through the measuring cell depends on the diffusion rate of the oxygen into the electrode and therefore is called a diffusion-limited current. (U.S. Pat. No. 3,691,023).

In order that the oxygen content of a gas be measured quantitively with the above-mentioned method, the measuring cell should be kept at a constant operating temperature of at least about 400° C., because the diffusion rate of gases depends heavily on temperature. This property of the measuring cell has a very detrimental effect in measuring operations, because it requires a very large amount of technical means to keep the desired temperature of the measuring cell constant to approximately ±2°-5° C.

SUMMARY OF THE INVENTION

It is therefore an object of the invention to provide a method and apparatus of the kind mentioned at the outset such that temperature variations have no appreciable influence on the measurement of the oxygen content. The amount of technical means required therefore is to be small and in particular, tolerable also for operational measurements.

With the foregoing and other objects in view, there is provided in accordance with the invention a method for determining the oxygen content in gases uninfluenced by temperature variations of the gases which comprises passing said gases into a first electrochemical measuring cell having a solid electrolyte which is heated to an operating temperature, and electrodes adjacent the electrolyte connected to a current source to obtain a diffusion-limited electric current flow which is dependent on the oxygen content of said gases, measuring the electric current flow as a first electrical signal imaging the oxygen content of the gases, passing an auxiliary gas with a constant oxygen content into a second electrochemical measuring cell of approximately the same design and under the same operating conditions as said first measuring cell, measuring the electric current flow in the second cell as a second electrical signal, and employing the quotient of said two electrical signals as a measure of the oxygen content of said gases, said measure of the oxygen content being uninfluenced by temperature variations of said gases.

In accordance with the foregoing, there is provided a measuring apparatus for determining the oxygen content in gases, such as exhaust gases, uninfluenced by temperature variations of the gases comprising a first electrochemical measuring cell having an oxygen ion-conducting solid electrolyte and a first electrode and a second electrode adjacent the surface of the electrolyte, a heater disposed near the solid electrolyte, conduit means for passing the feed gases in contact with said second electrode with diffusion of oxygen ion through said electrolyte to said first electrode and oxidation of the ions to molecular oxygen, electrical conducting leads connecting said first and second electrodes to an electric source to form an electric circuit through which flows an electric current as a function of the oxygen content of the feed gases, a second electrochemical measuring cell to be acted upon by an auxiliary gas of constant oxygen content, in comparison with the first measuring cell, having in the vicinity of the electrodes approximately the same dimensions, design and heater, the electrodes of the second cell are connected with a current source to form a second circuit and an electric current flows through the second circuit as a function of the auxiliary gas which contacts one electrode, and the two electric circuits connected to a divider for forming a quotient of signals from said first and said second electric currents in the two circuits.

Other features which are considered as characteristic for the invention are set forth in the appended claims.

Although the invention is illustrated and described herein as embodied in a method and apparatus for determining the oxygen content in gases, uninfluenced by temperature variations, it is nevertheless not intended to be limited to the details shown, since various modifications may be made therein without departing from the spirit of the invention and within the scope and range of equivalents of the claims.

BRIEF DESCRIPTION OF THE DRAWINGS

The invention, however, together with additional objects and advantages thereof will be best understood from the following description when read in connection with the accompanying drawings in which.

DETAILED DESCRIPTION OF THE INVENTION

In accordance with the invention, a second electrical signal is derived from the oxygen content of an auxiliary gas with constant oxygen content, using a second electrochemical measuring cell which is at least approximately identical with the first measuring cell as far as design, operation and operating conditions are concerned and that the quotient of the two electrical signals is formed and used as a measure for the oxygen content of the gas.

Since both measuring cells are at least approximately, or preferably completely, identical as far as operation, and in particular their temperature and their design are concerned, temperature variations act in both measuring cells as identical factors which are eliminated by the preferably automatic quotient formation. The measurement value so obtained is therefore independent of temperature variations. A prerequisite is merely that the temperature of the measuring cells do not drop below a minimum operating value which is at about 400° C. It should further be noted that the auxiliary gas is similar to the gas to be measured with respect to its chemical and physical properties. Thus, air can advantageously be used as the auxiliary gas for the determination of the oxygen content of combustion exhaust gases.

In one preferred device for carrying out the method, a first electrochemical measuring cell is provided with a heater. An oxygen ion-conducting electrolyte has electrodes which are connected to an electric current source to form an electric circuit. One electrode is acted upon by the gas and the electric current flowing as a function of the oxygen content of the gas can be measured. A second electrochemical measuring cell is provided which, in comparison to the first measuring cell, has at least in the region of the electrodes substantially about the same dimensions, approximately the same design as well as approximately the same heating system. The electrodes of the second measuring cell together with the current source are inserted into a second circuit. One of these electrodes is acted upon by the auxiliary gas which has constant oxygen content and the electric current flowing in the second circuit can be measured. The two electric circuits are connected to a divider for forming the quotient of the electrical current signals present in the two circuits, from there the quotient can be fed to an indicating instrument and/or a regulating or control device as a measure for the oxygen content of the gas.

Due to the preferably completely identical design of the two measuring cells as well as their identical heating system and their identical arrangement with respect to environment influence, any changes of both measuring cells that might occur proceed in the same direction and their effects on the formation of the quotient is eliminated. The formation of the quotient is accomplished here automatically in a preferably electronic divider which delivers the quotient signal which can be indicated as the oxygen content by an indicating instrument and/or can be used by a control or regulating device as a signal for regulating and/or controlling oxygen-dependent equipments.

One recommended further embodiment of the invention consists in arranging at least one adjustable variable resistor in the circuit connected to the second measuring cell. Thereby, optionally in cooperation with a similar control resistor in the circuit of the first measuring cell, a calibration of the measuring device can be performed and/or irregularities of the two measuring cells, for instance with respect to the construction of the electrodes and/or the heating system which may happen in spite of careful construction, assembly and operation can be compensated. If the first measuring cell comprises a tubular solid electrolyte which is provided on the inside and outside with electrodes and which is surrounded preferably concentrically by a heating tube, forming a first interspace, the second measuring cell, in a further embodiment of the invention, can be arranged in an extension of the heating tube with mirror symmetry to a symmetry plane which is perpendicular to the longitudinal axis of the interspace. The first interspace can be separated by at least one partition arranged in the symmetry plane from a second interspace, where each of the interspaces is closed off by a terminating wall from the outside space and has connections for the gas to be measured and the auxiliary gas, respectively. Thereby, a compact design is obtained and uniform heating of the two measuring cells is readily carried out. It is advantageous that the tubular solid electrolytes are closed off in the vicinity of the partition and their interior is in communication with the outside space.

Another embodiment of the measuring device according to the invention in which a first measuring cell has a tubular solid electrolyte with electrodes on the inside and the outside, consists in having the solid electrolyte of the second measuring cell and the solid electrolyte of the first measuring cell combined ine one piece. The outer electrodes of the two measuring cells adjoin an interspace provided with connecting openings. The interior of the solid electrolyte is in communication with the outside space. Thus, only a single tubular solid electrolyte is provided for both measuring cells, on which the electrodes are arranged. The electrodes arranged in the interior are preferably combined in a common one-piece electrode. The recommended arrangement of the heating element is in the interior of the tubular solid electrolyte.

One particularly preferred embodiment of the measuring device according to the invention consists in having the interspace of the first measuring cell and the interspace of the second measuring cell connected by a double-throw switching element to the gas sampling point or the auxiliary gas source, respectively, in such a manner that the interspaces can be acted on alternatingly by the gas to be measured and the auxiliary gas. By this arrangement, the function of the first and the second measuring cell can be mutually interchanged. This is recommended particularly if the gas carries along contaminations which could influence the porosity of the electrodes and thereby, the diffusion. In that case, uniform contamination of both measuring cells can be achieved by periodic interchange of the functions and thus the identity of both measuring cells can be kept up. In addition, the proper functioning of the cells can be checked by the interchange and if necessary, can be corrected by the control resistors. The same measurement value should be indicated before and after the switching if the oxygen content of the measuring gas is constant.

In order to, finally, assure sufficiently rapid supply of the gases to the electrodes, it is recommended that a preferably common suction device be inserted into the path of the gas to be measured and of the auxiliary gas.

Further advantages and features of the invention can be seen from the following description of embodiment examples in conjunction with the schematic drawing.

Like parts have the same reference symbols in the individual Figures. Futhermore, parts recurring in the individual Figures are provided with reference symbols only to the extent as this is necessary for an understanding.

Figure 1:
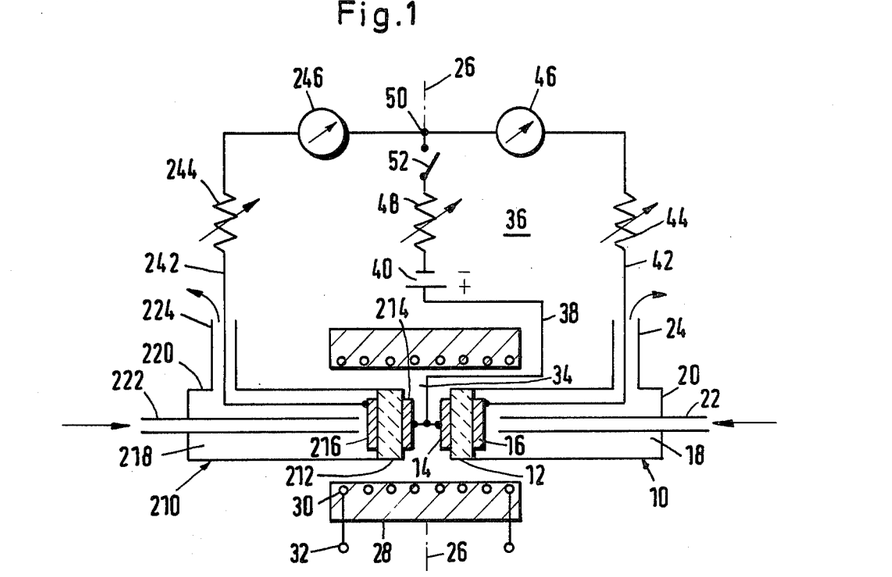
FIG. 1 shows the measuring device according to the invention with two measuring cells, in a longitudinal cross section, which have plate-shaped solid electrolytes.

The measuring device according to FIG. 1 shows a first measuring cell 10 with a disc-shaped solid electrolyte 12, on the one surface of which a first electrode 14 is arranged and on the opposite surface a second electrode 16. The solid electrolyte 12 consists, for instance, of calcium oxide which is doped with zirconium oxide so that the solid electrolyte is a good conductor for oxygen ions but it has little or no conductivity for electrons. The electrodes 14, 16 are formed as layers and are applied directly to the solid electrolyte. Material for the electrodes can be platinum or electrically conductive ceramic material. Sufficient porosity must be provided, so that gas can penetrate the electrodes to the solid electrolyte 12.

The second electrode 16 is surrounded by a space 18 which is formed in a housing 20. A feedline 22 opens into the space 18, near the second electrode 16, in such a way that the gas which is to be measured and is fed-in through the feedline 22 acts directly on the second electrode. A discharge line 24 through which the fed-in gas flows out after it has acted on the second electrode 16 is connected at the space 18. In order to prevent a short circuit between the inflowing and the outflowing gas, the connection of the discharge line 24 is arranged away from the mouth of the supply line 22.

As can further be seen from FIG. 1, a second measuring cell 210 is arranged with mirror symmetry to the first measuring cell 10. The symmetry plane 26 is perpendicular to the plane of the drawing of FIG. 1 and is parallel between and at a distance from that surface of the solid electrolyte 12 which carries the first electrode 14. The second measuring cell 210 is at least approximately identical but preferably completely identical with the first measuring cell 10. It therefore has a solid electrolyte 212 which is provided with the electrodes 214 and 216; the electrode 216 is adjacent to the space 218. This space 218 is formed in a housing 220 and is provided with a feedline 222 and a discharge line 224.

The first measuring cell 10 and the second measuring cell 210 are surrounded by a heater 28 which consists of a ceramic tube into which an electric heating coil 30 is embedded. Coil 30 has electrical leads 32. The heater 28 surrounds the measuring cells at a distance so that an annular space 34 remains between the measuring cells and the heater, which is open toward the outside so that ambient air acts on the electrodes 14 and 214. As can further be seen clearly from FIG. 1, the heater 28 is of mirror symmetrical and identical design with respect to the symmetry plane 26, so that the first measuring cell 10 and the second measuring cell 220 are heated equally when the heater is put in operation.

The first electrode 14 of the first measuring cell 10 is connected via an electrical lead 38 to the positive terminal of a current source 40 for d-c current, for instance in the form of an electric battery. The second electrode 16 is connected via the electrical lead 42 to the minus terminal of the current source 40. A variable resistor 44 is further inserted into the line 42 as is a current measuring device 46 in the form of a milliammeter, a switch 52 as well as an adjustable resistor 48, the sequence of these devices being counted from the second electrode 16. The electrodes 214, 216 of the second measuring cell 210 are connected to the current source 40 in the same manner. For this purpose, the first electrode 214 could be connected via a separate line to the current source 40, but it is simplest if this electrode is connected directly to the electric line 38 as can be seen from FIG. 1. The second electrode 216, on the other hand, has an electric line 242 which is run identically with the line 42 of the first measuring cell and into which accordingly a variable resistor 244 as well as a current measuring device 246 in the form of a milliammeter are inserted. Line 242 is connected to the current source 40 at the branching point 50 which is located after the variable resistor 48 as seen from the current source 40, so that resistor 48 is inserted into the circuit of the first measuring cell as well as into the circuit of the second measuring cell.

To measure the oxygen content of a gas with the measuring device according to FIG. 1, the measuring cells 10 and 210 are first heated by means of the heater 28 to the same operating temperature. A particular temperature value is not necessary; the operating temperature however, must be at least 400° C. Then the second electrode 16 which acts as the cathode is acted upon as the feedline 22 by the gas to be measured, which subsequently flows off through the discharge line 24.

At the same time, the second electrode 216 of the second measuring cell 210 is acted upon through the feedline 222 by an auxiliary gas which has constant oxygen content and is similar to the gas to be measured physically and chemically. The first electrodes 14 and 214 are in communication via the annular space 34 with the outside space 36, i.e. these electrodes are acted upon by ambient air.

An electric voltage is now applied to the electrodes of both measuring cells by closing the electric switch 52. The magnitude of this voltage is approximately 1 volt and can be adjusted by the resistor 48. The following now occurs in the two measuring cells; the oxygen of the gas and the auxiliary gas of the respective gases are reduced to oxygen ions by the second electrodes 16 and 216, respectively, which optionally have catalytic action. The oxygen ions penetrate the solid electrolyte 12 and 212, respectively, arrive at the first electrodes 14 and 214, respectively, and are oxidized there again to form oxygen molecules. The oxygen then flows off through the annular space 34 into the outside space 36. The electric currents flowing in accordance with the transport of the oxygen ions through the solid electrolyte, is measured by the current measuring devices 46 and 246, respectively.

The oxygen of the gas or the auxiliary gas get, through diffusion, into the second electrodes 16, 216. The amount of oxygen which diffuses into the electrodes per unit time, depends on the oxygen content of the gas and the auxiliary gas, respectively. Thus, the electric current of both measuring cells flowing with the oxygen ions depends on the amount of oxygen diffusing into the electrodes and, therefore, on the oxygen content of the gas and the auxiliary gas, respectively. The flowing electric current is therefore always diffusion-limited and is a measure for the oxygen content of the gas and the auxiliary gas.

Since diffusion processes are temperature-dependent, the measuring result depends on the temperature to which the first and the second measuring cell are heated. In order to eliminate this temperature influence, the quotient of the measurement results of the first measuring cell and the second measuring cell is used as the measure for the oxygen content of the gas to be measured, and not the reading of the current measuring device 46 which is associated with the first measuring cell. The oxygen content of the gas to be measured is determined by the following relation if the oxygen content of the auxiliary gas is known:

$$V = V_o \cdot I_2/I_1 \ [\%]$$

where

V = oxygen content of the gas to be measured [%]
$V_o$ = oxygen content of the auxiliary gas [%]
$I_2$ = electric current through the measuring cell acted upon by the gas to be measured (first measuring cell 10) [%]
$I_1$ = electric current flowing through the measuring cell acted upon by the auxiliary gas (second measuring cell 210) [%]

If ambient air is used as the auxiliary gas, the numerical value 20.95 is to be substituted for the oxygen content of the auxiliary gas.

Since the two measuring cells are of at least approximately identical design, temperature variations influence the flow of current through the two measuring cells in the same manner, so that their influence is cancelled in the formation of the quotient.

The measurement of the oxygen content is therefore independent of temperature variations of the measuring cells; it is only necessary that the temperature does not drop below a minimum operating temperature.

In FIG. 1 the current measuring devices 46 and 246 are inserted into the circuits which connect the measuring cells to the current source, so that from their reading the oxygen content of the gas to be measured can be determined by forming the quotient. This quotient is advantageously formed automatically as is shown in the embodiment examples according to FIGS. 2 and 3. It should also be noted that instead of a single current source 40, to which both measuring cells are connected, each measuring cell can have its own current source.

In order that differences in the construction of the two measuring cells, for example with respect to the thickness and/or the pore structure of the electrodes and/or in the heating, can be compensated, the control resistors 44 and 244 are arranged in the circuits of the individual measuring cells. With these resistors, the current flow in the circuits can be influenced and irregularities of the two measuring branches can be compensated. For this purpose, an auxiliary gas with constant oxygen content is fed to the two measuring cells and the control resistors 44 and 244 are adjusted so that the two current measuring devices 46, 246 show the same measurement value. The measuring circuits of the two measuring cells are now matched to each other and are ready for the measurement.

It is also advisable to perform the above-described balancing of the measuring circuits during the operation of the measuring device, for instance daily or at daily or weekly intervals in order to compensate for non-uniform aging or, for instance, changes of the porosity of the electrodes.

Figure 2:
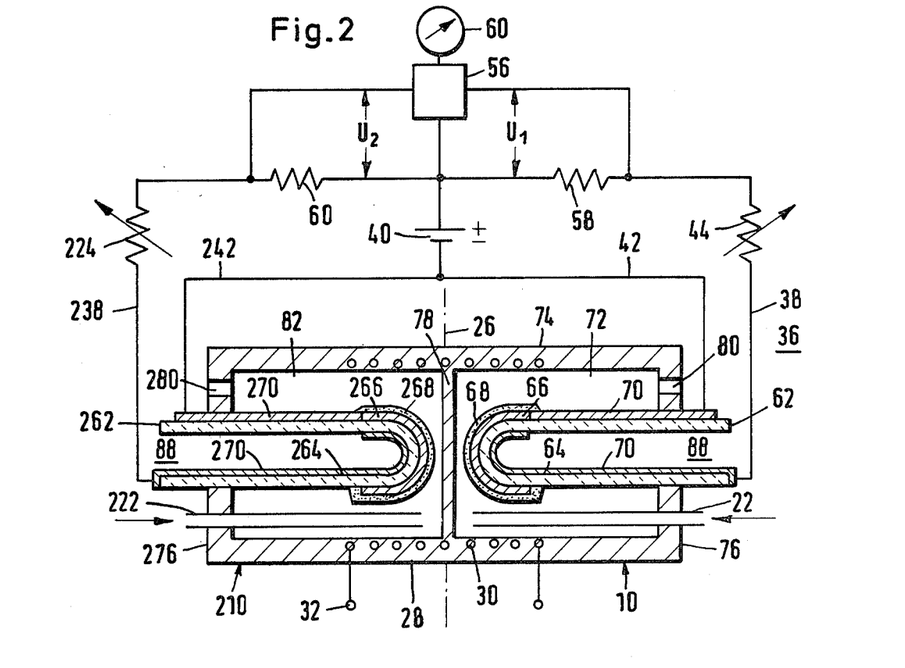
FIG. 2 is an embodiment variant of the subject of FIG. 1 with measuring cells, in a longitudinal cross section, which have tubular solid electrolytes.

In FIG. 2, a further embodiment of the measuring device according to the invention is shown. The first measuring cell 10 has a tubular solid electrolyte 62 with a closed-off end, while the other end is open. The solid electrolyte 62 has in the interior, near its closed end, a first electrode 64, and the outside is provided with the second electrode 66 which additionally has a porous coating 68 in the form of layer which determines the diffusion of the gas to the electrode. To the respective electrodes 64, 66, strip-like conductor runs 70 are connected which lead to the open end region of the solid electrolyte 62 and serve as electrical terminals. The tubular solid electrolyte 62 protrudes, centered, into an intermediate space 72 which has preferably a circular cross section. The interspace is formed by a heating tube 74 which consists of ceramic material and is provided with an electric heater 28 in the form of a heating coil 30. The interspace 72 is closed-off from the outside by a terminating wall 76 which has a central opening in which the solid electrolyte tube 62 is fastened. In the vicinity of the closed end of the solid electrolyte tube 62, the interspace 72 is closed off by a transverse partition 78. The feedline 22 is brought in the axial direction into the interspace 72 up to the vicinity of the partition 78 through the end wall 76 and diametrically thereto, an outlet opening 80 is provided in the terminating wall 76.

In mirror symmetry to the plane 26 which is perpendicular to the longitudinal axis of the interspace 72 or the solid electrolyte tube 62 and has the thickness of the partition 78, there is provided in a mirror-symmetrical axial extension of the heater tube 74 a second interspace 82 in which a second tubular solid electrolyte 262 is arranged. The latter is provided with a first inner electrode 264, a second electrode 266, a coating 268 arranged thereon as well as with conductor runs 270 which are all at least approximately of identical design with the corresponding components of the solid electrolyte tube 62 of the first measuring cell. Also the second interspace 82 is provided with a feedline 222 through a terminating wall 276 and an outlet opening 280. In summary, it can be said that the second measuring cell 210 together with the heater tube is of identical design with the first measuring cell 10.

As in the embodiment example according to FIG. 1, the electrodes of the two measuring cells are connected via electrical lines 38, 42, 238, 242 to a current source 40, with control resistors 44 and 244 inserted into the line branches 42, 242. Instead of the current measuring devices 46, 246 of the embodiment example according to FIG. 1, a divider 56 is provided in the present case, in which the quotient of the electric currents flowing in the circuits is formed automatically. Dividers of this kind are known in electronics and are described, for instance, in the book "Electronik", second part: Industrial Electronics, edited by vocational instructors and engineers, third edition, published by Europa-Lehrmittel, 5600 Wuppertal 2, Kleiner Werth 50.

On page 171, in paragraph 8.2.3., the circuit diagram of such a divider is shown. Accordingly, this divider is designed for forming quotients from two electric voltages. So that this divider can now be used in the present embodiment example, in which current values are divided into each other, these current values must be converted into voltage values. This purpose is served by the electric resistor 58 which is inserted into the circuit of the first measuring cell, and by the resistor 60' which is inserted into the circuit of the second measuring cell. The electric currents flowing in the two circuits cause voltage drops at the resistors 58 and 60', respectively, which are proportional to the flowing current and therefore image the current of the circuits. The voltage drop which takes place at the respective resistors 58, 60' is fed to the electric inputs of the divider 58 as the input voltages $U_1$ and $U_2$. In the divider 56, the quotient is formed from these input voltages and is delivered as an electrical voltage value and indicated by a connected indicating instrument 60. This scale of said device can be calibrated directly in volume percent of oxygen content, so that the oxygen content is indicated directly.

The operation of the measuring device according to FIG. 2 is the same as with the measuring device according to the embodiment example of FIG. 1. Accordingly, the gas to be measured is introduced into the interspace 72 via the feedline 22, where it passes to the outside through the outlet opening 80 after it has acted upon the coating 68. At the same time, the first electrode 64 of the first measuring cell 10 through its interior 88 is in communication with the outside space 36, so that the oxygen transported through the solid electrolyte 62 can be discharged to the outside.

In the same manner, the auxiliary gas with constant oxygen content, preferably air, is conducted via the feedline 222 into the second interspace 82 of the second measuring cell and, after it has acted on the coating 268, is conducted through the outlet opening 280 to the outside 36, while the first electrode 264 is likewise in communication with the outside space. After the voltage is applied to the electrodes of the two measuring cells, the oxygen content of the gas to be measured can be read at the indicating instrument 60.

Here too, the control resistors 44, 244 serve for calibrating the measuring device or for equalizing differences between the first and the second measuring cell. To perform the calibration, the same test gas is fed to the first measuring cell 10 and the second measuring cell 210, and the control resistors 44, 244 are set so that the known oxygen content of the test gas is indicated by the indicating instrument 60.

It would, of course, also be possible to insert into the lines 42, 242 the current measuring devices 46, 246 as in the embodiment example according to FIG. 1, and perform the balancing as described there.

Figure 3:
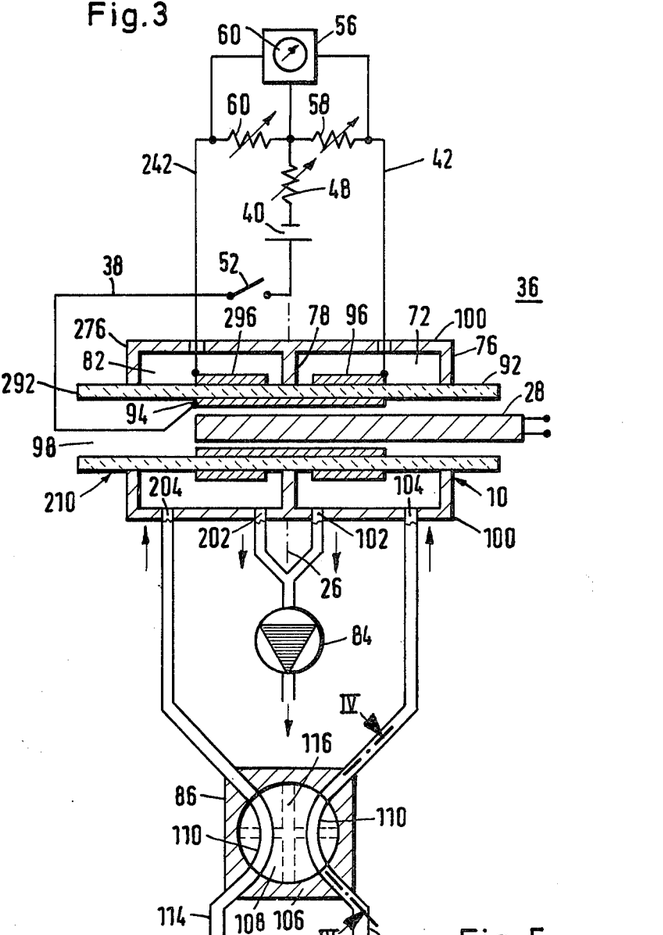
FIG. 3 is a further embodiment variant of the subject of the invention with measuring cells, in a longitudinal cross section, which have a common solid electrolyte tube.

The variable resistors 44, 244 in the embodiment example according to FIG. 2 are not required if the resistors 58, 60' are made variable so that the calibration or the balancing of the circuits can be made with these resistors 58, 60' as is shown, for instance, in the embodiment example of FIG. 3.

FIG. 3 shows an embodiment variant of the electrochemical measuring device according to FIG. 2. Essential differences from the embodiment according to FIG. 2 are that the tubular solid electrolyte 92 of the first measuring cell 10 and the solid electrolyte 292 of the second measuring cell 210 consist of one piece, i.e. both solid electrolytes consist of a single tube open at the end, in the interior 98 of which the heater 28 is arranged in the form of an electric heating rod. Also, the first electrodes arranged in the interior of the solid electrolytes are combined to form a common continuous electrode 94. The outer electrodes 96 and 296 are arranged, as in the embodiment example according to FIG. 2, in the respective interspaces 72 and 82 which are separated from each other by a partition 78 which is perpendicular to the longitudinal axis of the tubular solid electrolyte 92. The overall design here is also mirror-symmetrical to the symmetry plane 26 which has the thickness of the partition 78.

The electric circuit of the measuring cell is in accordance with the preceding embodiment examples, with the indicating instrument 60 built into the divider 56 in the present case.

The periphery of the housing 100, consisting of ceramic refractory material, has a circular cross section and surrounds the interspaces 72, 82, connecting openings 102, 104, 202, 204, axially spaced for the supply and discharge of the auxiliary gas and the gas to be measured. The connecting openings 102, 202, through which the gas to be measured and the auxiliary gas, respectively, are discharged from the interspaces 72 and 82, are connected to a suction device 84 in the form of a pump, which assures an adequate gas stream passing through the interspaces 72, 82.

The connecting opening 104, through which the gas to be measured is fed, as well as the connecting opening 204 through which the auxiliary gas is fed-in, are connected via interposed pipelines to a switching element 86, for instance, in the form of a switching valve. This switching element 86 allows the gas to be measured to be fed at will to the first measuring cell 10 or to the second measuring cell 210, with simultaneous changing of the auxiliary gas supply. Periodic switching, for instance, at interval of days, is advisable for long-term measurement if the gas to be measured carries dirt particles which lead to a change of the porosity of the electrode or the coating, because through the change of the mode of operation of the two measuring cells, uniform contamination of both electrodes 96, 296 is achieved and the requirement as to the identity of both measuring cells is met over extended periods.

Figure 5:
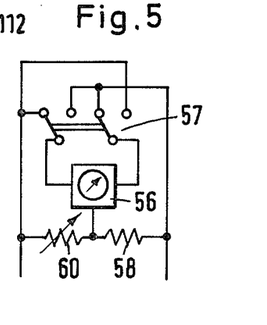
FIG. 5 shows a variant of FIG. 4 particularly with reference to a double-throw switch.

By switching, the operation of the two measuring cells 10 and 210 can also be checked because with a measuring gas having constant oxygen content, for instance air, the same measurement value must be indicated before and after the switching. For this purpose, however, it is necessary that with the switching of the gas supply, the connections of the divider 56 are also switched in order to ensure the correct formation of the quotient. In FIG. 5, a detail of FIG. 3, is shown how such a switching of the connection can be carried out. The main component is an electric double-throw switch 57 which is built into the two leads which carry the signals to be divided and by which the connections can be interchanged. It is advantageous to couple the electric double-throw switch 57 to the switching element 86 so that the gas-supply switching of the divider 56 is automatically coupled to the switching of the gas supply.

Figure 4:
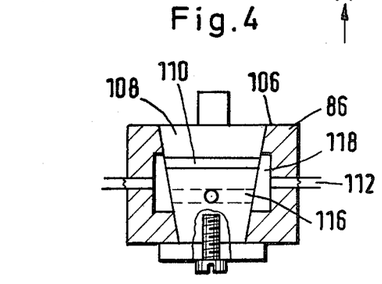
FIG. 4 shows a detail of the switching valve of FIG. 3 in cross section taken along the line IV-IV.

The design of the switching element 86 can be seen clearly from the cross section shown in FIG. 3 in conjunction with the vertical cross section shown in FIG. 4. The conical rotatable insert 108 is provided in the valve housing 106. This insert 108 has connecting canals in two planes (see FIG. 4). The connecting canals 110 have the form of an arc and connect, in the position shown in FIG. 3 of the insert 108, the measuring gas line 112 to the connecting opening 104 of the first measuring cell 10 as well as the auxiliary gas line 114 to the connecting opening 204 of the second measuring cell 210. If the insert 108 is rotated 45°, the connections are interchanged: For, in that case the connecting canals 110 are not operative and the connecting canals 116 which go through the inset 108 in cross-fashion now connect the measuring gas line 112 to the connecting opening 204 of the second measuring cell 210 as well as the auxiliary gas line 114 to the connecting opening 104 of the first measuring cell 210. This position of the insert 108 is not shown in the drawings. Since the connecting canals 110 and 116 are arranged in two different planes, vertical recesses 118 are provided in the valve housing 106 for the supply of the gas or the discharge of the gas, respectively.

Figure 6:
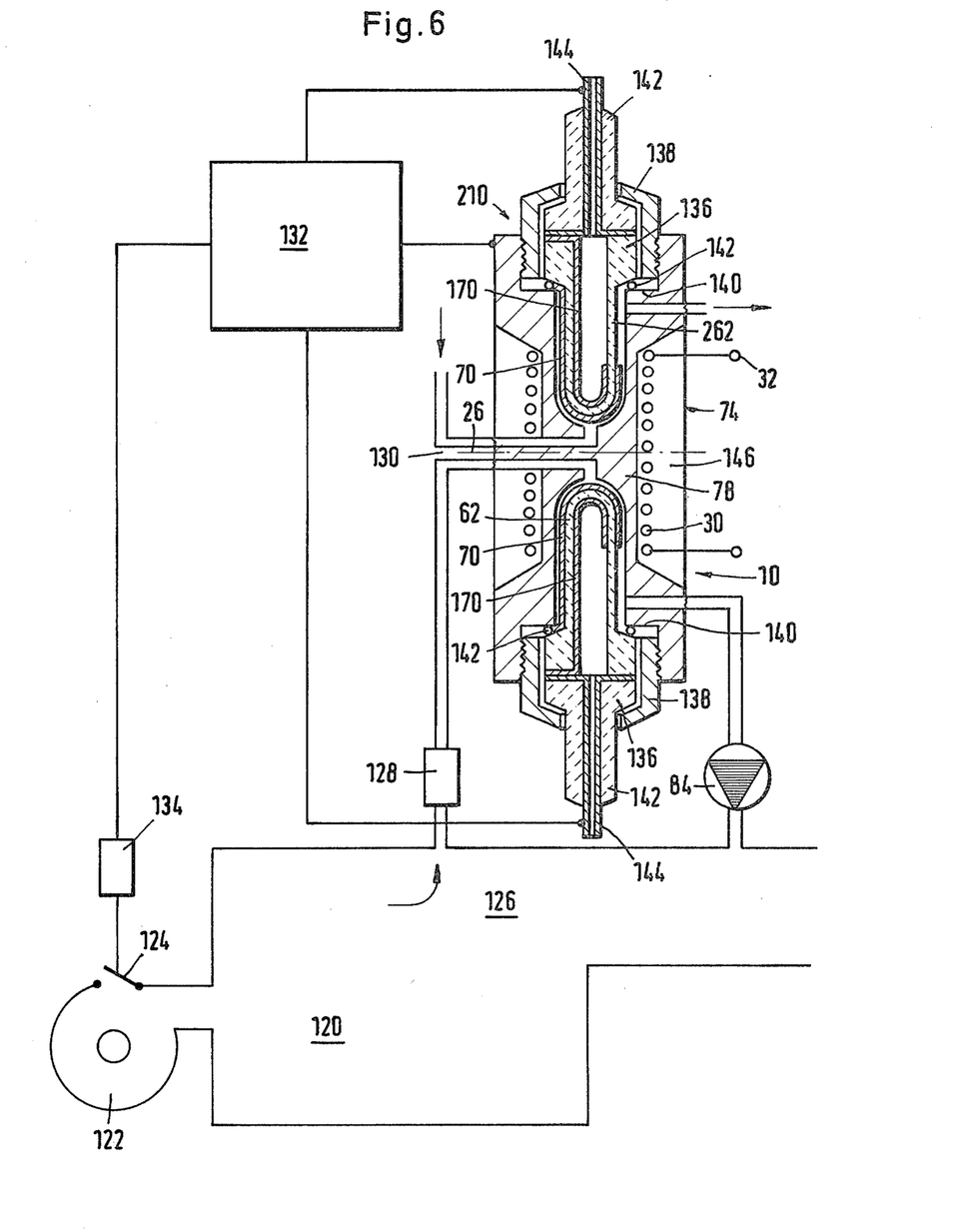
FIG. 6 is an embodiment variant of the subject of the invention with respect to the measuring cells as well as their use for the combustion control of a burner.

FIG. 6 shows an embodiment of the invention in connection with a fire box 120. The latter consists of a boiler for fluid fuels, for instance, oil, with a burner 122, the opening of which can be varied for drawing-in combustion air through a damper 124. Exhaust gas is taken from the exhaust gas canal 126 of the fire box and fed to the first measuring cell 10 with the interposition of a gas filter 128. After flowing through the first measuring cell, the gas is returned to the exhaust gas canal 126 while an interposed suction device 84, for instance in the form of a pump, maintains the gas stream through the first measuring cell 10.

Outside air flows through the second measuring cell 210 and serves as the auxiliary gas. In order to provide for the possibility of alternating the operation of the two measuring cells 10 and 210, a switching element 86 as was described in connection with FIGS. 3 and 4 can be inserted at the point 130.

The two measuring cells are connected to a regulating or control device 132 which contains the resistors required for balancing or calibrating the individual measuring circuits, as well as the divider provided for the formation of the quotient as well as the power supply. In addition, a set-point can be set into the regulating or control device 132, with which the oxygen content measured in the exhaust gas is compared. Upon a deviation of the measured value from the set value, the regulating or control device 132 delivers a signal to a positioning device 134 which changes the air throttle 124 of the burner 122 until the set-point value agrees with the oxygen content of the combustion exhaust gases.

By influencing the air supply to the combustion, it is possible to optimize the combustion since for an economical operation of the fire box 120, the oxygen content of the combustion exhaust gases should be as low as possible. Continuous monitoring and regulation is necessary mainly because the output of the combustion air blower arranged in the burner 122 changes if the air pressure changes and thereby influences the combustion.

The measuring cells according to the embodiment example, according to FIG. 6, are of a design similar to that of a measuring cell according to the embodiment example as per FIG. 2. Differences relate substantially to the manner of fastening the tubular solid electrolytes 62, 262 in the heating tube 74, which in the present case consists of ceramic which is electrically conductive. In the present case, the solid electrolytes each have at their open end a shoulder 136 which is pressed by a screw connection 138 in the form of a screw cap against a step 140 of the heating tube 74, with the interposition of an electrically conducting sealing ring 142. The conductor run 70 leading away from the outer electrode is pressed against the shoulder so that the connection for the current supply to the outer electrodes can be made via the heating tube 74.

In the interior of the screw connection 138, plunger-like inserts 132 with a central hole are provided which go through the screw connection 138 to the outside and which are pressed by the inward-pointing edge of the screw connection 138 against the shoulder 136 of the solid electrolyte tube. In the hole of the plunger 132, tubular electric conductors 144 are provided which extend over the end face of the plunger 132 and are connected with the conductor run 170 which extends in the interior of the solid electrolyte tube and is connected to the inner electrode, and which extends also over the end face of the shoulder 136. The current can, therefore, be supplied to the inner electrode via the respective electric conductors 144.

In the region of the electrode, the heating tube 74 has an external circular recess 146, on which the electric heating coil 30 is wound. In order to avoid heat losses, the recess 146 can be filled with insulating material after the heating coil has been wound.

The measuring cells 10 and 210 and the heating tube 74 are constructed symmetrically to the plane of symmetry 26, which halves the partition 78 between the two measuring cells. The partition 78 is made thick in relation to the diameter of the heating tube so that the canals through which the gas to be measured and the auxiliary gas is fed to the measuring cells run in this partition 78 and lead directly to the tip of the closed solid electrolyte tube.

The following dimensional values apply for the design of the individual measuring cells:

In FIG. 1, the thickness of the solid electrolytes is about 0.5 to 2 mm, and the electrodes have a surface area of 0.5 to 5 $cm^2$, beyond which the solid electrolyte extends at least 1 mm. In FIG. 2, the outside diameter of the tubular solid electrolyte is about 5 to 25 mm with a wall thickness of about 0.5 to 2 mm and a length of about 20 to 200 mm. The radial distance between the electrode and the heater tube 74 is about 0.5 to 5 mm. The area of an electrode is about 0.5 to 10 $cm^2$. For FIG. 3, approximately the same values apply with an overall length of the tubular solid electrolyte of about 40 to 200 mm. In the embodiment according to FIG. 6, the above-mentioned values apply similarly. The shoulder 136 of the tubular solid electrolyte always has a diameter which is about 1.5 to 2-times the outside diameter of the solid electrolyte.

I claim:

1. Method for determining the oxygen content in gases influenced by temperature variations of the gases which comprises passing said gases in contact with a first electrochemical measuring cell connected to a voltage source, said electrochemical cell having a solid electrolyte which is heated to an operating temperature, and through which a diffusion-limited electric current flows which depends on the oxygen content of the gases and the magnitude of which is determined as a first electrical signal measuring the oxygen content of the gases, the combination therewith of deriving a second electrical signal from the oxygen content of an auxiliary gas with a constant oxygen content by passing the auxiliary gas in contact with a second electrochemical measuring cell which is approximately identical to the first measuring cell with respect to design, operation and operating conditions to obtain said second electrical signal, and forming a temperature-independent quotient from the two electrical signals and employing the quotient as a measure of the oxygen content of the gases, wherein a heater is disposed in the first measuring cell to heat the electrolyte which is an oxygen ion-containing solid electrolyte, a first electrode adjacent an inside surface of the electrolyte and a second electrode adjacent the opposite outside surface, said electrodes connected to the voltage source to form an electric circuit, with one of said electrodes acted on by said gases causing an electric current which flows as a function of the oxygen content of said gases, wherein the second measuring cell also has a solid electrolyte with electrodes on the inside and outside surfaces of the electrolyte, wherein the solid electrolytes of the first and the second measuring cells consist of one piece, wherein the outer electrode for the first cell and for the second cell each is surrounded by an interspace with openings for the introduction and discharge for the feed gases and the auxiliary gas, wherein the interspace of the first cell is connected to said gases and the interspace of the second cell is connected to the auxiliary gas with a double-throw switching device to enable switching the flow of gases from the first interspace to the second interspace and the flow of auxiliary gas from the second interspace to the first interspace and the reverse, wherein the electrodes of the second cell are connected to the voltage source to form a second electric circuit, with said auxiliary gas acting on one of said electrodes causing an electric current to flow in the second circuit as a function of the oxygen content of the auxiliary gas, wherein the two electric circuits are connected to a divider for forming the quotient of said two determined electric current signals, and wherein the temperature-independent quotient is fed to a receiving device acting as an indicating, regulating or controlling device.

2. Method according to claim 1, wherein the interior of the solid electrolyte is in communication with the ambient atmosphere, and wherein a common heater heats both cells.

3. Method for determining the oxygen content in gases influenced by temperature variations of the gases which comprises passing said gases in contact with a first electrochemical measuring cell connected to a voltage source, said electrochemical cell having a solid electrolyte which is heated to an operating temperature, and through which a diffusion-limited electric current flows which depends on the oxygen content of the gases and the magnitude of which is determined as a first electrical signal measuring the oxygen content of the gases, the combination therewith of deriving a second electrical signal from the oxygen content of an auxiliary gas with a constant oxygen content by passing the auxiliary gas in contact with a second electrochemical measuring cell which is approximately identical to the first measuring cell with respect to design, operation and operating conditions to obtain said second electrical signal, and forming a temperature-independent quotient from the two electrical signals and employing the quotient as a measure of the oxygen content of the gases, wherein a heater is disposed in the first measuring cell to heat the electrolyte which is an oxygen ion-conducting solid electrolyte, a first electrode adjacent an inside surface of the electrolyte and a second electrode adjacent the opposite outside surface, said electrodes connected to the voltage source to form an electric circuit, with one of said electrodes acted on by said gases causing an electric current which flows as a function of the oxygen content of said gases, wherein the second measuring cell also has a solid electrolyte with two electrodes on the inside and outside surfaces of the electrolyte wherein the second cell has, as compared to the first cell, in the vicinity of the electrodes, approximately, the same dimensions, the same design and the same heater, wherein the electrodes of the second cell are connected to the voltage source to form a second electric circuit with said auxiliary gas acting on one of said electrodes causing an electric current to flow in the second circuit as a function of the oxygen content of the auxiliary gas, wherein the two electric currents are connected to a divider for forming the quotient of said two determined electric signals, and wherein the temperature-independent quotient is fed to a receiving device acting as an indicating, regulating or controlling device, wherein the solid electrolyte of the first cell is tubular, wherein the heater is a heating tube surrounding the electrolyte forming a first interspace, wherein the second measuring cell is arranged in an extension of the heating tube as a mirror image of the first cell with respect to a mirror plane which extends perpendicularly to the longitudinal axis of the interspace, wherein the first interspace is separated by a partition arranged in the mirror plane from a second interspace, wherein each of the interspaces is closed off from the outside by a terminating wall, and wherein each wall has inlets for the introduction of the gases and the auxiliary gas, respectively.

4. Method according to claim 3, wherein the tubular solid electrolytes are each closed off at one end in the vicinity of the partition, and the other ends of the electrolytes are in communication with the outside space.

* * * * *